(12) United States Patent
McCrone

(10) Patent No.: US 8,159,339 B2
(45) Date of Patent: Apr. 17, 2012

(54) CHILD MONITORING SYSTEM

(76) Inventor: Audrey McCrone, Peotone, IL (US)

(*) Notice: Subject to any disclaimer, the term of this patent is extended or adjusted under 35 U.S.C. 154(b) by 442 days.

(21) Appl. No.: 12/052,810

(22) Filed: Mar. 21, 2008

(65) Prior Publication Data
US 2009/0237238 A1    Sep. 24, 2009

(51) Int. Cl.
*G08B 1/08*    (2006.01)

(52) U.S. Cl. ........... 340/539.15; 340/539.1; 340/539.12; 340/539.13; 340/573.4; 340/7.2; 370/313; 455/41.2

(58) Field of Classification Search .. 340/539.1–539.32, 340/573.4; 370/312; 455/41.2
See application file for complete search history.

(56) References Cited

U.S. PATENT DOCUMENTS

| | | | |
|---|---|---|---|
| 2002/0190861 A1* | 12/2002 | Wentworth | 340/568.1 |
| 2005/0157668 A1* | 7/2005 | Sivan | 370/312 |
| 2007/0030155 A1* | 2/2007 | Van Woudenberg | 340/573.1 |
| 2007/0236344 A1* | 10/2007 | Desrosiers et al. | 340/539.15 |

* cited by examiner

*Primary Examiner* — George Bugg
*Assistant Examiner* — Ojiako Nwugo
(74) *Attorney, Agent, or Firm* — Michael Ries

(57) ABSTRACT

Disclosed is a child monitoring system. The child monitoring system includes a plurality of caregiver units and a child monitoring unit. The child monitoring unit is communicably coupled to the plurality of caregiver units and the plurality of caregiver units are configured to communicate amongst each other. The child monitoring unit is configured to detect an audible sound of the child. A signal responsive of the audible sound of the child is generated and transmitted to at least one caregiver unit of the plurality of caregiver units. Further, the child monitoring unit is configured to receive a signal responsive of instructions of the at least one caregiver of the plurality of caregivers from the at least one caregiver unit.

7 Claims, 3 Drawing Sheets

CHILD MONITORING SYSTEM

FIELD OF THE INVENTION

The present invention relates to child monitoring systems, and more particularly, to a child monitoring system utilizing a bidirectional communication.

BACKGROUND OF THE INVENTION

Caregivers, such as parents, of a child always keep the child on their forefront to take care of the child and to ensure the child's routine needs are addressed. There may be a possibility that sometime the parents may skip the child's care and routine needs due to involvement in other activities or because they are not present around the child. However, to ensure the child's care, there are nurseries and daycare centers where children stay so that their routine needs and care may be addressed by a professional caregivers. Putting the child in the nurseries may not solve the aforesaid problem as the professional caregivers of the nurseries may also skip a particular child's care and his/her routine needs due to involvement with other children in the nurseries. Moreover, keeping the child in nurseries may be costly for the parents as well.

To avoid keeping the child in a nursery and to insure proper care of the child at places such as at home several child monitoring systems are known in the art. Such a typical child monitoring system monitors the child and helps a caregiver to take care of the routine needs of the child. However, these child monitoring systems are unidirectional monitoring systems. For example, these child monitoring systems allow the parents to listen to noises made by their children by a one way communication, and to act accordingly for the child. With such a unidirectional monitoring system, the parents can only listen the noise made by the child but cannot reciprocate back to instruct the child or the caregiver in order to take care of the child.

Accordingly, there is a need for a child monitoring system that may help in insuring the child's care and routine needs of the child to be done on time without putting the child in a nursery. Further, the child monitoring system should be capable of facilitating the parents or the caregivers to reciprocate back to the child upon listening to a noise made by the child. Furthermore, the child monitoring system should also facilitate the caregivers, such as parents of the child, in communicating with each in order to fulfill the requirements of the child.

SUMMARY OF THE INVENTION

In view of the foregoing disadvantages inherent in the prior art, the general purpose of the present invention is to provide a child monitoring system that is configured to include all advantages of the prior art, and to overcome the drawbacks inherent therein.

Therefore, an object of the present invention is to provide a child monitoring system that is capable of facilitating a caregiver of a child to listen an audible sound generated by the child, and simultaneously facilitating the caregiver to communicate to another caregiver of the child, to fulfill needs of the child.

Another object of the present invention is to provide a child monitoring system that is capable of facilitating parents or caregivers of a child to communicate to the child.

Therefore, in an aspect, the present invention provides a child monitoring system for monitoring a child and facilitating communication between a plurality of caregivers of the child. The child monitoring system comprises a plurality of caregiver units and a child monitoring unit. The plurality of caregiver units is capable of being held by the plurality of caregivers of the child. The plurality of caregiver units is configured to facilitate communication between the plurality of caregivers. The child monitoring unit is capable of communicating to the plurality of caregiver units. The child monitoring unit is configured to detect an audible sound of the child. Based on the audible sound of the child, a signal responsive of the audible sound of the child is generated and transmitted to at least one caregiver unit of the plurality of caregiver units. Further, the child monitoring unit is configured to receive a signal responsive of instructions of the at least one caregiver of the plurality of caregivers from the at least one caregiver unit, based on the audible sound of the child.

In another aspect, the present invention provides a child monitoring unit for monitoring a child. The child monitoring unit is configured to communicate with a plurality of caregiver units to receive instructions of at least one of the plurality of caregivers. The child monitoring unit comprises a microphone, a transceiver and a speaker. The microphone detects an audible sound of the child. A signal responsive of the audible sound is detected by the microphone and then transmitted by the transceiver, to at least one caregiver unit of the plurality of caregiver units. Based on the audible sound, a signal responsive of the instructions of the at least one caregiver of the plurality of caregivers from at least one caregiver unit of the plurality of caregiver unit is received by the transceiver. Further, based on the signal responsive of the instructions, the instruction is released by the speaker. The instructions of the at least one caregivers are then followed by the child.

These together with the other aspects of the present invention, along with the various feature of novelty that characterized the present invention, are pointed out with particularity in the claims annexed hereto and form a part of the present invention. For a better understanding of the present invention, its operating advantages, and the specified object attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which:

Like reference numerals refer to like parts throughout the description of several views of the drawings.

DETAILED DESCRIPTION OF THE INVENTION

For a thorough understanding of the present invention, reference is to be made to the following detailed description, including the appended claims, in connection with the above-described drawings. Although the present invention is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting.

The term "first", "second", "rear", "front" and the like, herein do not denote any order, quantity or importance, but rather are used to distinguish one element from another, and the terms "a" and "an" herein do not denote a limitation of quantity, but rather denote the presence of at least one of the referenced item.

The term "caregivers" used herein include parents of a child and individuals, other than the parents, who take care of the child.

The present invention provides a child monitoring system for monitoring a child. The child monitoring system utilizes a bidirectional communication that facilitates a communication between a caregiver of a plurality of caregivers and the child, and amongst the plurality of the caregivers.

Figure 1:
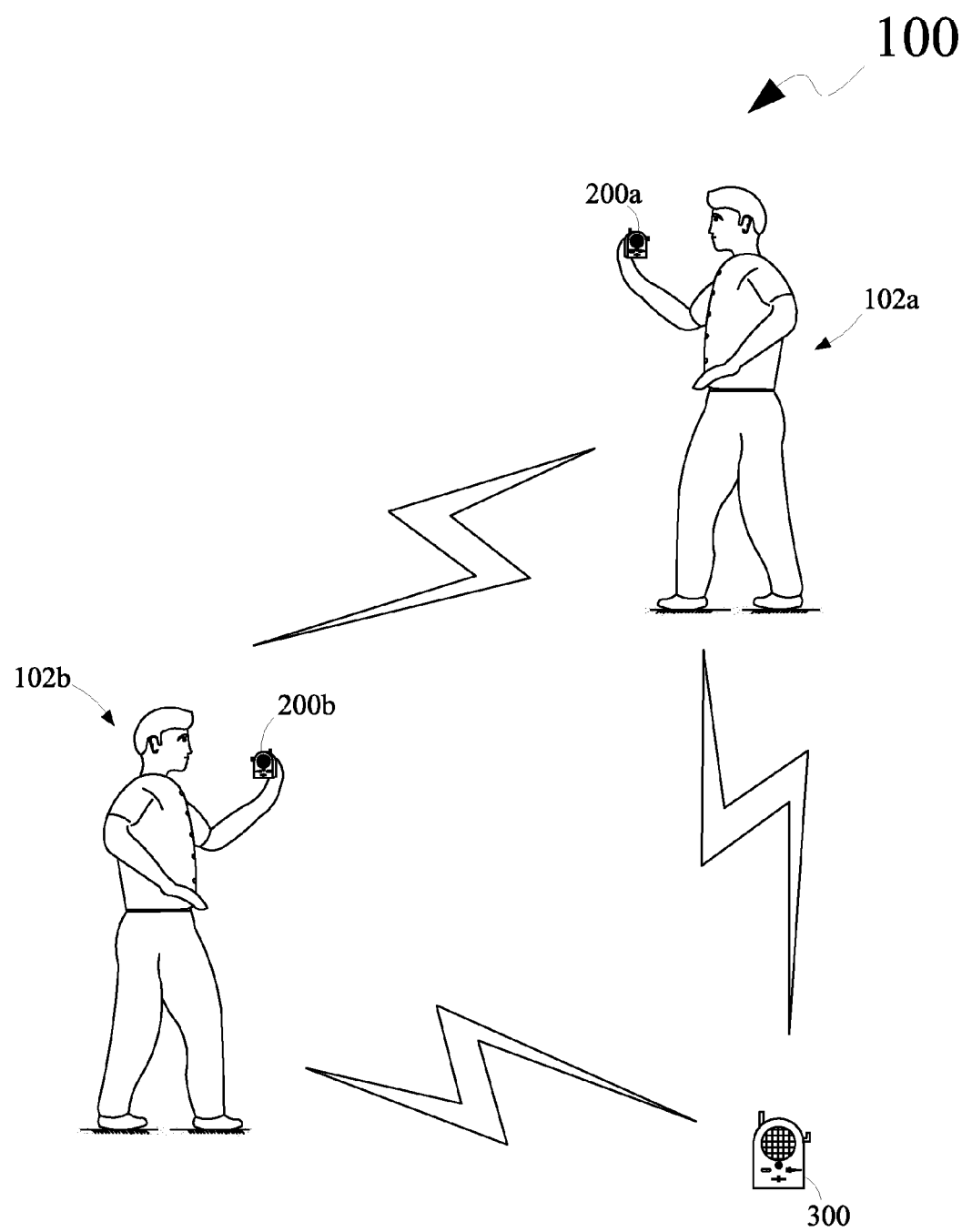
FIG. 1 is a schematic illustration of a child monitoring system, according to an exemplary embodiment of the present invention.

Referring now to FIG. 1, a schematic illustration of the child monitoring system, such as a child monitoring system 100, according to an exemplary embodiment of the present invention is shown. The child monitoring system 100 includes a plurality of caregiver units, such as, a first caregiver unit 200a and a second caregiver unit 200b, and a child monitoring unit 300. The child monitoring unit 300 is placed in a child's room. The first caregiver unit 200a and the second caregiver unit 200b are used by a plurality of caregivers, such as a first caregiver 102a and a second caregiver 102b, respectively. The child monitoring unit 300 may be communicably coupled to the first caregiver unit 200a of the first caregiver 102a and to the second caregiver unit 200b of the second caregiver 102b.

In a case when the child is small enough that he/she may not be able to take care of him/herself, the child monitoring unit 300 detects an audible sound of the child. Further, in an embodiment of the present invention, the child monitoring unit 300 transmits a signal responsive of the audible sound of the child to at least one caregiver unit, for example, the first caregiver unit 200a. The first caregiver unit 200a is carried by the first caregiver 102a. The first caregiver 102a listen the audible sound of the child through the first caregiver unit 200a. There may be situations when the first caregiver 102a is not present around the child or is busy in other activities, and as such the first caregiver 102a may not be able to fulfill the requirements of the child. To fulfill the requirements of the child, the first caregiver 102a may communicate to the second caregiver 102b at the second caregiver unit 200b, which is carried by the second caregiver 102b. The second caregiver 102b being communicated by the first caregiver 102a about the requirements of the child may take required steps to fulfill the requirements of the child.

In another embodiment of the present invention, the child monitoring unit 300 after detecting the audible sound of the child, transmits the signal responsive of the audible sound of the child to each of the first caregiver unit 200a and to the second caregiver unit 200b. On listening the audible sound of the child, the first caregiver 102a having the first caregiver unit 200a and the second caregiver 102b having the second caregiver unit 200b may communicate to each other, in order to fulfill the requirements of the child. This bidirectional communication between the first caregiver 102a and the second caregiver 102b is capable of fulfilling the requirements of the child by the first caregiver 102a or the second caregiver 102b, whosoever, is around the child.

In another case, when the child is able to take care of him/her self based on instructions given by the first caregiver 102a or the second caregiver 102b, the child may directly communicate to any of the first caregiver 102a and the second caregiver 102b. More specifically, the child monitoring unit 300 detects an audible sound of the child and transmits a signal responsive of the audible sound of the child to at least one caregiver unit, for example, the first caregiver unit 200a. The first caregiver 102a listen the audible sound of the child through the first caregiver unit 200a and instructs the child at the child monitoring unit 300 to perform an action. Further, in another embodiment, the child monitoring unit 300 may also transmit the signal responsive of the audible sound of the child to the first caregiver unit 200a and to the second caregiver unit 200b at a same time, in response of which either of the first caregiver 102a or the second caregiver 102b may instruct to the child. Alternatively, the first caregiver 102a and the second caregiver 102b may communicate to each other and then instruct to the child at the child monitoring unit 300. This bidirectional communication between the child monitoring unit 300 and the first caregiver 102a and the second caregiver 102b facilitates to fulfill the requirements of the child.

Figure 2:
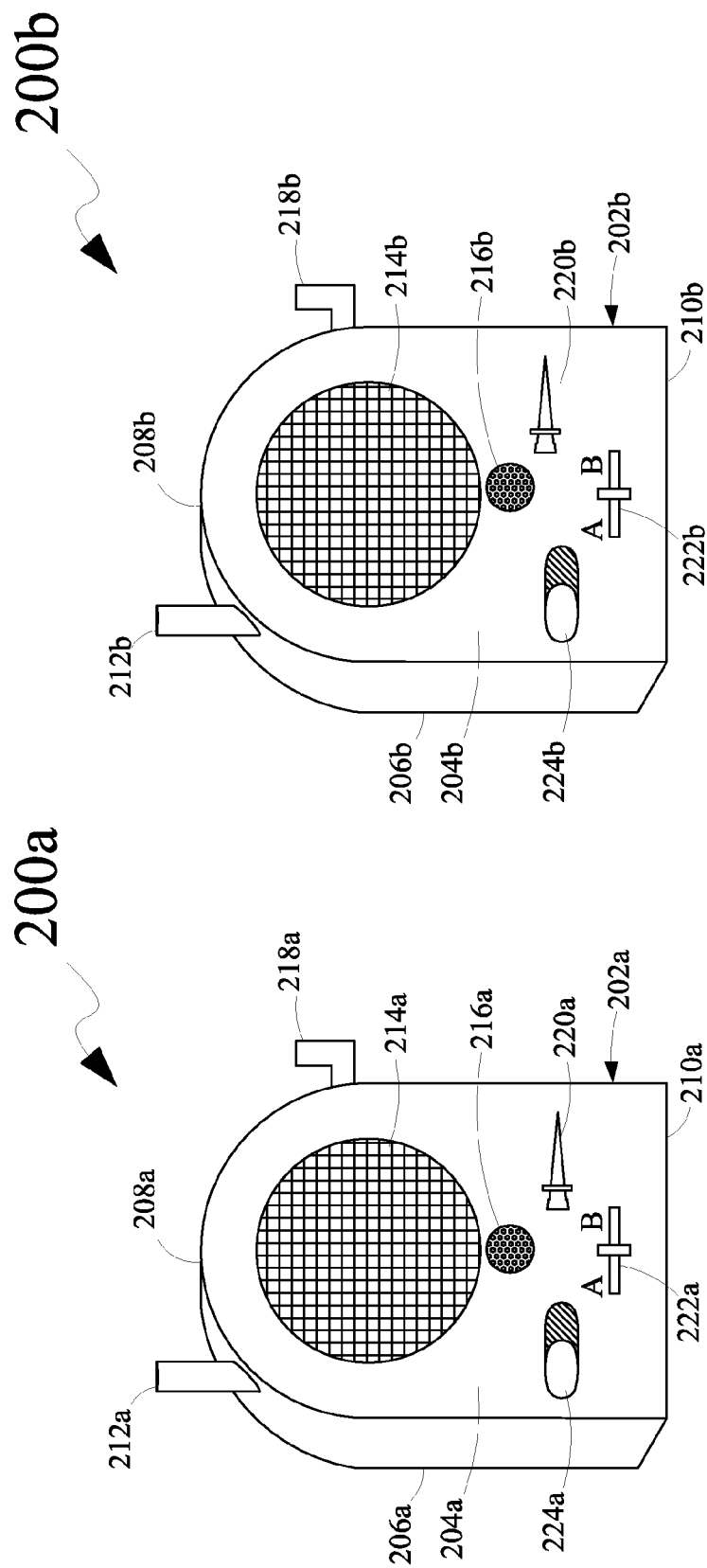
FIGS. 2A and 2B are perspective views of a plurality of caregiver units of the child monitoring system, according to an embodiment of the present invention.

Now referring to FIGS. 2A and 2B, perspective views of the first caregiver unit 200a and the second caregiver unit 200b of the child monitoring system 100, are shown.

Referring to FIG. 2A in particular, the first caregiver unit 200a includes a housing 202a, a speaker 214a, a microphone 216a, a transceiver (not shown) and a button 218a. The speaker 214a, the microphone 216a, and the transceiver are configured within the housing 202a, and the button 218a may be disposed onto the housing 202a.

The housing 202a, as shown in FIG. 2A, is for the exemplary purposes only and should not be considered limiting in any way. The housing 202a includes a front portion 204a and a rear portion 206a. The housing 202a has a circular top portion 208a and a planar base 210a. The planar base 210a of the housing 202a facilitates the first caregiver unit 200a to be placed on a support structure, such as a table, a nightstand or a dresser in a first caregiver's room. Further, the housing 202a may be substantially compact, so that the first caregiver 102a may carry the first caregiver unit 200a in a convenient manner. The transceiver is configured to receive the signal responsive to the audible sound of the child. The speaker 214a is configured to release the audible sound of the child to the first caregiver 102a. The first caregiver 102a may instruct the required steps to be taken in response to the audible sound of the child. Accordingly, the first caregiver 102a may provide the instruction to the transceiver through the microphone 216a.

The microphone 216a is further configured to transmit the signal responsive to the instructions given by the first caregiver 102a to the child monitoring unit 300. More specifically, the first caregiver unit 102a may include an antenna 212a, which may be a bidirectional antenna configured to transmit and receive the signal for the communication between the first caregiver unit 200a and the child monitoring unit 300. In one embodiment, the antenna 212a may be installed at the circular top portion 208a of the housing 202a, however it will be apparent to those ordinary skilled in the art that the antenna 212a may also be installed at any suitable place of the housing 202a.

Referring particularly to FIG. 2B, the second caregiver unit 200b is shown. The second caregiver unit 200b is similar to the first caregiver unit 200a in terms of the configurations and the appearances. For example, the second caregiver unit 200b includes a housing 202b, a transceiver (not shown), a speaker 214b, a microphone 216b and a button 218b. The housing 202b is similar to the housing 202a of the first caregiver unit 200a. The housing 202b has a front portion 204b and a rear portion 206b. In an exemplary embodiment, the housing 202b has a circular top portion 208b and a planar base 210b. The purposes of the planar base 210b is similar to the planar base 210a, as the planar base 210b provides the second caregiver unit 200b to be placed on a suitable place, for example, in the second caregiver's room. The transceiver is configured to communicate to the child monitoring unit 300. Similar to the first caregiver unit 200a, the second caregiver unit 200b also includes an antenna 212b, which is same in terms of configuration and the purposes of the antenna 212a. Further, configurations and the purposes of the speaker 214b and the microphone 216b of the second caregiver unit 200b is same as the speaker 214a and the microphone 216a of the first caregiver unit 200a.

Further, the first caregiver unit 200a and the second caregiver unit 200b are also configured to communicate to each other. More specifically, the transceivers of the first caregiver unit 200a and the second caregiver unit 200b may communicate to each other through the antenna 212a and the antenna 212b respectively. This communication is needed in cases when the first caregiver 102a and the second caregiver 102b want to consult each other about giving instructions to the child or to take required steps for the care of the child.

The first caregiver unit 200a and the second caregiver unit 200b may communicate to each other by using the buttons 218a and 218b, respectively. The button 218a may be disposed onto a lateral side of the housing 202a of the first caregiver unit 200a. Similarly, the button 218b may also be disposed onto a lateral side of the housing 202b of the second caregiver unit 200b. The buttons 218a and 218b are configured to facilitate the communication between the first caregiver unit 200a and the second caregiver unit 200b. For example, after listening to the audible sound of the child, the first caregiver 102a may press the button 218a to initiate the communication with the second caregiver unit 200b in order to consult the second caregiver 102b. Specifically, on pressing the button 218a, a communication channel is set up between the first caregiver unit 200a and the second caregiver unit 200b. Similarly, the second caregiver 102b may communicate to the first caregiver 102a by pressing the button 218b, when the second caregiver 102b receives the audible sound from the child monitoring system 300.

Further, each of the first caregiver unit 200a and the second caregiver unit 200b may include a volume control mechanisms 220a and 220b and channel mechanisms 222a and 222b, respectively. The volume control mechanisms 220a and 220b are configured to increase or decrease the volumes of the audible sound and the instructions. The first caregiver unit 200a and the second caregiver unit 200b may also includes power switches 224a and 224b in order to switch ON or switch OFF the first caregiver unit 200a and the second caregiver unit 200b, respectively. The power switches 224a and 224b may be positioned at the front portions 204a and 204b, respectively. The first caregiver unit 200a and the second caregiver unit 200b may be powered by a battery (not shown) or by electricity. The channel mechanisms 222a and 222b are configured to switch channel between a channel A and a channel B, in case of interference of the audible sound of the child, and the instructions given by the first caregiver unit 200a and the second caregiver unit 200b, or a message exchange between the first caregiver unit 200a and the second caregiver unit 200b.

In another embodiment of the present invention, a particular channel may be dedicated to a communication between the two entities. Further, the channel mechanisms 222a and 222b may be linked to the buttons 218a and 218b, respectively. For example, when the channel mechanism 222a is at channel A, the first caregiver unit 200a may communicate to the child monitoring unit 300 and when the channel mechanism 222b is at channel B, the first caregiver unit 200a may communicate to the second caregiver unit 200b. It will be apparent to a person skilled in the art that in this embodiment, the first caregiver 102a may press the button 218a to switch the channel mechanism 222a from the channel A to the channel B.

Figure 3:
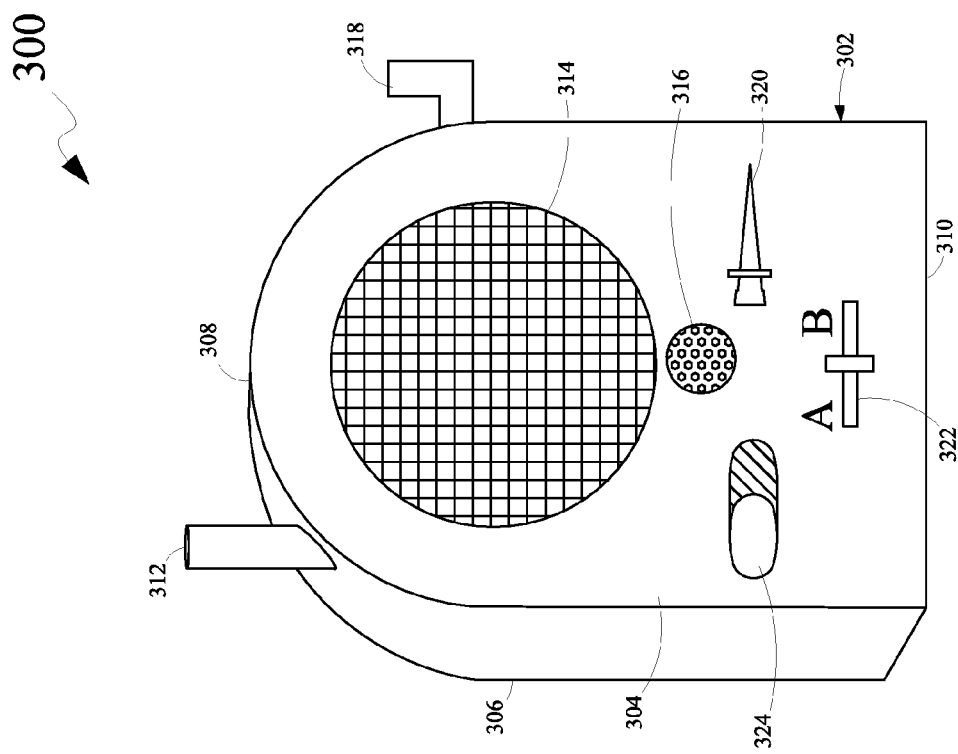
FIG. 3 is a perspective view of a child monitoring unit of the child monitoring system, according to an embodiment of the present invention.

Referring now to FIG. 3, a perspective view of the child monitoring unit 300 of the child monitoring system 100 is shown.

The child monitoring unit 300 includes a transceiver (not shown), a speaker 314, a microphone 316 and a button 318. The transceiver, the speaker 314 and the microphone 316 may be accommodated within a housing 302. The child monitoring unit 300 is also similar to the first caregiver unit 200a and the second caregiver unit 200b in terms of the configuration. The housing 302 is composed of a front portion 304 and a rear portion 306. In an exemplary embodiment, the housing 302 includes a circular top portion 308 and a planar base 310, which facilitates the child monitoring unit 300 to be placed on a support structure, such as a table, a nightstand or a dresser in the child's room. The transceiver of the child monitoring unit 300 is configured to transmit the audible sound generated by the child by the help of an antenna 312 to at least one of the first caregiver unit 200a and the second caregiver unit 200b. In one embodiment, the antenna 312 may be installed at the circular top portion 308 of the housing 302. However, it will be apparent to those ordinary skilled in the art that the antenna 312 may also be installed at any suitable place of the housing 302.

Further the transceiver is configured to receive the signals responsive to the instructions of the first caregiver 102a and the second caregiver 102b from the first caregiver unit 200a and the second caregiver unit 200b, respectively, through the antenna 312. In one embodiment, the antenna 312 may be a bidirectional antenna in order to transmit signals in response of the audible sound of the child to the first caregiver unit 200a and the second caregiver unit 200b, and to receive the signals in response to the instructions of the first caregiver 102a or the second caregiver 102b. The speaker 314 and the microphone 316 are functionally similar to the speakers 214a and 214b, and the microphone 216a and 216b, respectively. For example, the microphone 316 is configured to provide a signal responsive to the audible sound of the child to the transceiver, which is further communicated to at least one of the first caregiver unit 200a or the second caregiver unit 200b. The speaker 314 is configured to provide the instructions obtained from the first caregiver unit 200a and the second caregiver unit 200b in an audible form to the child or any person sitting near the child.

In one embodiment of the present invention, the button 318 of the child monitoring unit 300 may be used to select a communication link for example, a choice between a caregiver unit of the first caregiver unit 200a and the second caregiver unit 200b. The button 318 may be provided at a lateral side of the housing 302. The button 318 may be pressed for initiating the communication between the child monitoring unit 300 to the first caregiver unit 200a and the second caregiver unit 200b. The child monitoring unit 300 further includes a volume control mechanism 320, a channel mechanism 322 and a power switch 324 couple to the front portion 304 of the housing 302. The volume control mechanism 320 is similar to the volume control mechanisms 220a and 220b. In an embodiment of the present invention, the channel mechanism 322 is configured to facilitate a switching a channel A to a channel B or vice versa, in case of interference of the audible sound of the child, and the instructions given by the first caregiver unit 200a and the second caregiver unit 200b. In another embodiment of the present invention, the channel mechanism 322 may be configured in a manner such that, when the channel mechanism 322 is on the channel A, the child monitoring unit 300 may communicate to the first caregiver unit 200a. Similarly, when the channel mechanism 322 is on the channel B, the child monitoring unit 300 may communicate to the second caregiver unit 200b. Further, the power switch 324 is configured to switch ON or switch OFF the child monitoring unit 300. The child monitoring unit 300, like the plurality of caregiver units may be powered by a battery (not shown) or by electricity.

Referring again to FIGS. 1 to 3, operations performed within the child monitoring system 100 may be explained as follows. The child monitoring unit 300 is capable of communicating with the first caregiver unit 200a and the second caregiver unit 200b to receive instructions of at least one of the first caregiver 102a or the second caregiver 102b. The child monitoring unit 300 detects an audible sound of the child by the microphone 316. The audible sound is received by the transceiver of the child monitoring unit 300. A signal responsive of the audible sound is generated by the transceiver. Further, the signal responsive of the audible sound is transmitted by the transceiver of the child monitoring system 100 through the antenna 312 to a caregiver unit, for example, to the first caregiver unit 200a.

The signal responsive of the audible sound is received by the transceiver of the first caregiver unit 200a through the antenna 212a. Accordingly, the speaker 214a provides the audible sound to the first caregiver 102a. Similarly, the audible sound may also be received by the second caregiver unit 200b. On listening the audible sound, any one of the first caregiver 102a or the second caregiver 102b may instruct to the child monitoring unit 300. The instructions of the first caregiver 102a and the second caregiver 102b may be transmitted by the antenna 212a and the antenna 212b of the first caregiver unit 200a and the second caregiver unit 200b, respectively. On listening to the instructions, when the child is capable of taking care of him/her self, the child may follow the instructions of at least one the first caregiver 102a or the second caregiver 102b.

Further, the child monitoring unit 300 may transmit the signal responsive of the audible sound of the child to each of the first caregiver unit 200a and to the second caregiver unit 200b, in a similar manner as explained above. On listening to the audible sound of the child, the first caregiver 102a and the second caregiver 102b may communicate to each other by pressing the buttons 218a, 218b and 318, respectively. Accordingly, the first caregiver 102a and the second caregiver 102b may take requited steps for the care of the child. The communication between the first caregiver 102a and the second caregiver 102b may be advantageous in situations when the child is not capable of taking care of him/herself. In such case, the first caregiver 102a and the second caregiver 102b may coordinate between each other such that at least one of them may go to take care of the child.

Various embodiments of the present invention offer following advantages. The present invention provides a child monitoring system, such as, the child monitoring system 100. The child monitoring system provides a bidirectional communication between a child monitoring unit such as the child monitoring unit 300 and between the plurality of caregiver units such as the first caregiver unit 200a and the second caregiver unit 200b. The child monitoring system is capable of facilitating a caregiver of the child to listen an audible sound generated by the child, and simultaneously facilitating the caregiver to communicate to another caregiver of the child, in order to fulfill the requirements of the child. Further, the child monitoring system is capable of facilitating the child to communicate to the caregivers to take instructions from the caregivers to fulfill his/her requirements. The child monitoring system utilizing the bidirectional communication facilitates the caregivers to fulfill the requirements of the child without putting the child into the nurseries.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, to thereby enable others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present invention.

What is claimed is:

1. A child monitoring system to monitor a child by a plurality of caregivers and a plurality of caregiver units, comprising:
 a first caregiver unit;
 at least one second caregiver unit, each of the second caregiver units specific to at least one caregiver of the plurality of caregivers, the second caregiver units configured to communicate amongst each other, wherein each said caregiver unit includes;
 a housing;
 a speaker configured within the housing to release the audible sound of the child;
 a microphone configured within the housing to detect the instructions of the at least one caregiver of the plurality of caregivers;
 a transceiver coupled to the housing configured to receive the signal responsive of the audible sound of the child, transmit the signal responsive of the instructions of the caregiver to the child monitoring unit, and communicate to at least one caregiver unit of the plurality of caregiver units;
 a button coupled onto the housing, the button configured to select a caregiver unit of the plurality of caregiver units to communicate to the caregiver unit;
 a child monitoring unit capable of communicating to the caregiver units, the child monitoring unit configured to, detect an audible sound of the child, transmit a signal responsive of the audible sound of the child to the first caregiver unit of the plurality of caregiver units, and receive a signal responsive of instructions of the at least one caregiver of the plurality of caregiver units from the second caregiver unit, wherein the child monitoring unit includes;

a housing configured to accommodate the microphone, the transceiver and the speaker;

a microphone configured within the housing to detect the audible sound of the child;

a speaker configured within the housing to release the instructions of the at least one caregiver of the plurality of caregivers;

a transceiver coupled to the housing configured to, transmit the signal responsive of the audible sound of the child to the at least one caregiver unit of the plurality of caregiver units, and receive the signal responsive of the instructions of the at least one caregiver of the plurality of caregiver units from the at least one caregiver unit;

a button coupled onto the housing, the button configured to select a caregiver unit of the plurality of caregiver units to communicate to the caregiver unit; and a bidirectional antenna provided on the caregiver units and the child monitoring unit wherein the caregiver units are in bidirectional communication with the child monitoring unit.

2. The child monitoring system of claim 1, wherein the each caregiver unit of the plurality of caregiver units further comprises a volume control mechanism to control a volume of the released audible sound of the child.

3. The child monitoring system of claim 1, wherein the each of the plurality caregiver units further comprises a channel mechanism, wherein the channel mechanism is configured to allow the each caregiver unit to switch channels in case of an interference of the audible sound of the child and the instructions of the plurality of caregivers.

4. The child monitoring system of claim 1, wherein the each caregiver unit of the plurality of caregiver units further comprises a power switch coupled on the housing.

5. The child monitoring system of claim 1, wherein the child monitoring unit further comprises a volume control mechanism to control a volume of the released instructions of the at least one caregiver.

6. The child monitoring system of claim 1, wherein the child monitoring unit further comprises a channel mechanism, wherein the channel mechanism is configured to enable the child monitoring unit to switch channels in an interference of the instructions of the at least one caregiver.

7. The child monitoring system of claim 1, wherein the child monitoring unit further comprises a power switch disposed on the housing.

* * * * *